(12) United States Patent
Kyseliov

(10) Patent No.: US 10,045,822 B2
(45) Date of Patent: Aug. 14, 2018

(54) VETERINARY ORTHOPEDIC KIT

(71) Applicant: Ihor Heorhiovych Kyseliov, Sevastopol (UA)

(72) Inventor: Ihor Heorhiovych Kyseliov, Sevastopol (UA)

(73) Assignee: Ihor Heorhiovych KYSELIOV, Sevastopol (UA)

(*) Notice: Subject to any disclaimer, the term of this patent is extended or adjusted under 35 U.S.C. 154(b) by 0 days.

(21) Appl. No.: 14/765,918

(22) PCT Filed: Jul. 15, 2013

(86) PCT No.: PCT/UA2013/000075
§ 371 (c)(1),
(2) Date: Aug. 5, 2015

(87) PCT Pub. No.: WO2014/123503
PCT Pub. Date: Aug. 14, 2014

(65) Prior Publication Data
US 2015/0366616 A1  Dec. 24, 2015

(30) Foreign Application Priority Data

Feb. 7, 2013   (UA) .................... 201301454

(51) Int. Cl.
*B65D 69/00* (2006.01)
*B65D 71/00* (2006.01)
(Continued)

(52) U.S. Cl.
CPC .......... *A61B 19/0264* (2013.01); *A61B 50/30* (2016.02); *A61D 1/00* (2013.01);
(Continued)

(58) Field of Classification Search
CPC ............ A61B 19/0271; A61B 19/0256; A61B 19/0264; A61B 50/30; A61D 1/00
(Continued)

(56) References Cited

U.S. PATENT DOCUMENTS

| 4,750,905 A * | 6/1988 | Koeneman .......... A61F 2/30965 623/23.51 |
| 2011/0071572 A1* | 3/2011 | Sixto .................. A61B 17/8875 606/286 |
| 2012/0209265 A1* | 8/2012 | Pool .................... A61B 17/1725 606/55 |

FOREIGN PATENT DOCUMENTS

| CN | 201920920 U | 8/2011 |
| RU | 2206290 C2 | 6/2003 |

(Continued)

OTHER PUBLICATIONS

Ilizarova. Tekhnicheskoe opisanie i instruktsia po ekspluatatsii, Gudermes, CHIASSR, 1978 [on-line] [retrieved on Oct. 23, 2013]. Found in Internet: <URL:http://woikin.narod.ru/medtehnika/apparat_ilizarova.pdf.
(Continued)

*Primary Examiner* — Rafael Ortiz
(74) *Attorney, Agent, or Firm* — Leason Ellis LLP

(57) ABSTRACT

The veterinary orthopedic kit relates to veterinary science and more specifically to orthopedics and traumatology, and can be used in veterinary clinics in the treatment and restoration of function to damaged limbs of dogs, cats and other animals. The technical problem to be solved consists in the timely and quality provision of emergency care to injured animals, an increase in the effectiveness of treatment and the prevention of serious complications. This problem is solved in that orthopedic external fixation systems are provided in a universal and multifunctional set. The veterinary orthopedic kit consists of a rectangular container in the
(Continued)

Figure 1:
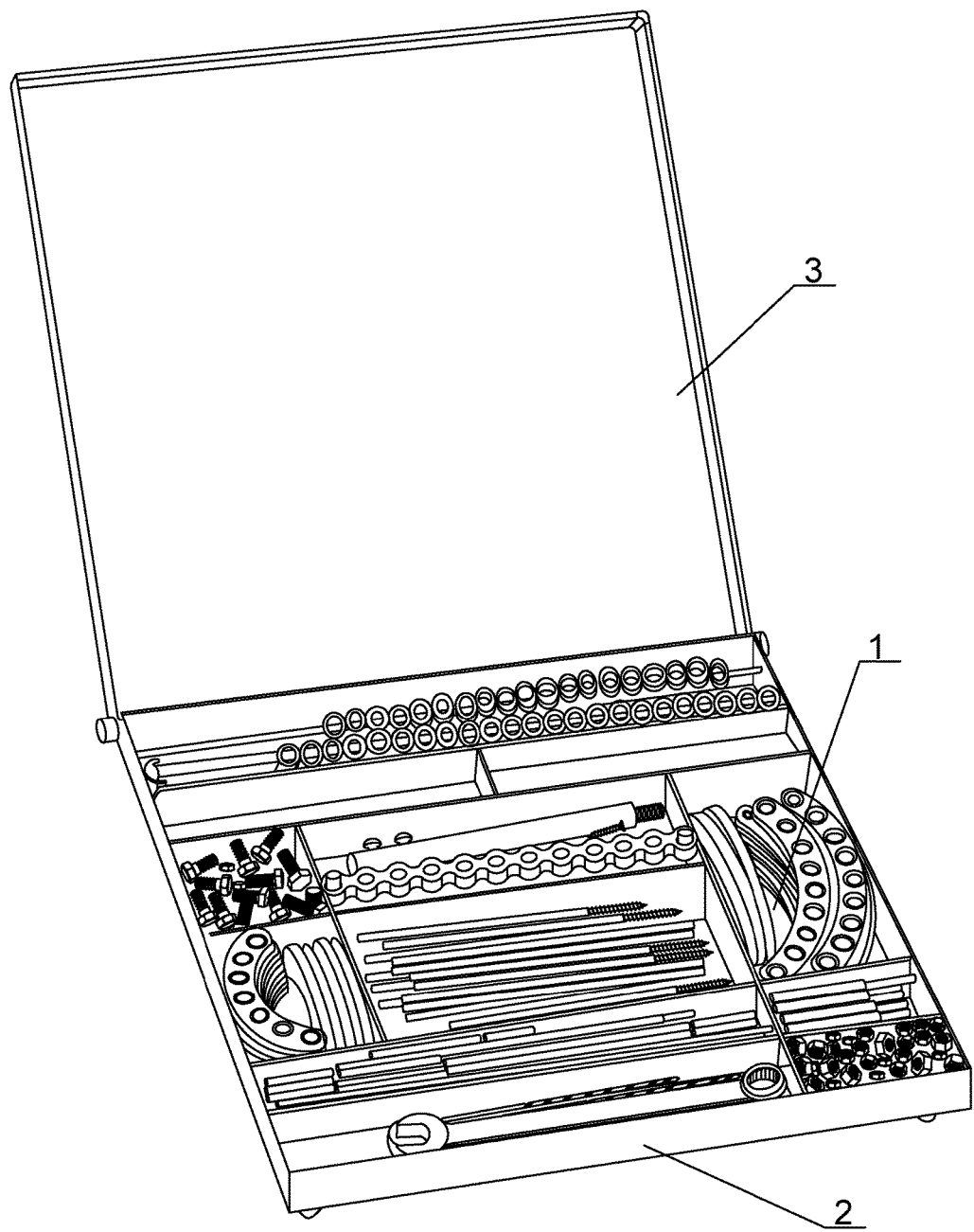

form of a box having a lid and being divided by partitions into a plurality of sections. The sections accommodate a set of components and instruments for the purposes of external fixation: polyfunctional monoblocks, plates, rods and pins, bars, fasteners and instruments.

6 Claims, 2 Drawing Sheets

(51) Int. Cl.
*A61B 19/02* (2006.01)
*A61D 1/00* (2006.01)
*A61B 50/30* (2016.01)
*A61B 17/56* (2006.01)
*A61B 50/00* (2016.01)

(52) U.S. Cl.
CPC ....... *A61B 17/56* (2013.01); *A61B 2050/0056* (2016.02); *A61B 2050/3008* (2016.02)

(58) Field of Classification Search
USPC ..... 206/572, 363, 370, 373, 438; 606/53, 54
See application file for complete search history.

(56) References Cited

FOREIGN PATENT DOCUMENTS

| UA | 53478 U | 10/2010 |
|---|---|---|
| UA | 70025 U | 5/2012 |

OTHER PUBLICATIONS

International Search Report in corresponding PCT Application No. PCT/UA2013/000075 and and Written Opinion, dated Nov. 21, 2013; International Preliminary Report dated Aug. 11, 2015.

* cited by examiner

VETERINARY ORTHOPEDIC KIT

CROSS-REFERENCE TO RELATED PATENT APPLICATIONS

This application is a U.S. National Phase Application under 35 U.S.C. § 371 of International Patent Application No. PCT/UA2013/000075, filed Jul. 15, 2013, and claims the priority of Ukraine Application No. U 2013 01454, filed Feb. 7, 2013, all of which are incorporated by reference in their entireties. The International Application was published on Aug. 14, 2014 as International Publication No. WO 2014/123503 A1.

FIELD

The invention is related to veterinary medicine, and more specifically to orthopedics and traumatology (external fixation systems). This kit can be used in veterinary hospitals in treatment and restoration of damaged limb function in dogs, cats and other animals.

RELATED ART

At present, for treatment of diaphyseal fractures of long bones of limbs in small family animals, in particular dogs and cats, in many cases are used traditional conservative (plaster bandages, splints) and operational (extramedullary and intraosteal anchors) methods for bone immobilization that do not always ensure an accurate reposition and stable rigid fixation of bone fragments throughout the entire treatment. Traumas during surgery on osteogenic tissues (periosteum, bone marrow), and also on surrounding soft tissues and bone feeding vessels result in various complications, and as a consequence, prolong the time of healing. The method of transosseous osteosynthesis, developed by G. A. Ilizarov, as well as similar methods of other authors, applied to bone fractures of different etiology, severity and location, made it possible to create conditions for a favorable course of reparative osteogenesis and positive outcome of treatment. Yet these technical and technological possibilities of treatment for limb bone fractures in small home animals in some cases are not justified and require the development of new methods of osteosynthesis, systems and techniques due to the fact that:
  universal versions of layout of external osteosynthesis devices for treatment of limb long bones, depending on species, age and sex of home animals, location and the nature of a fraction have not been adequately developed;
  existing devices do not provide for accurate repositioning of bone fragments and their stable fixation until fracture healing and deformity correction are complete, and surgical intervention in the area of the fracture is required.

There are known [see WWW document]. URL: http://reko-med.ru (Jan. 9, 2013) products for orthopedics which include various orthopedic products used in modern treatment and rehabilitation programs in traumatology and orthopedics. The disadvantage is that these products make it possible to achieve precise reposition of bone fragments yet do not provide for their stable fixation, since they are not designed for application in veterinary medicine.

There is a need for a comprehensive veterinary orthopedic set which would increase efficiency of contemporary hi-tech surgical intervention procedures in treatment and restoration of damaged limbs of dogs, cats and other animals.

This utility model entitled Veterinary Orthopedic Kit meets the above requirement, making it possible for a specialist in the field of veterinary surgery and orthopedics, equipped with a set of required external fixation orthopedic systems in a compact package, to provide timely and quality treatment to injured animals, to improve efficiency of treatment, and to prevent the development of serious complication.

This result is achieved due to the fact that the suggested veterinary orthopedic kit is designed for application in various clinical cases in veterinary practice. All components of the kit can be used multiple times (except for consumables). Increased efficiency of surgical intervention is provided by application of specially designed and assembled universal and multifunctional orthopedic devices.

DISCLOSURE OF INVENTION

The veterinary orthopedic kit comprises (FIG. 1) a rectangular container 1 made in the form of a box 2 with a lid 3, which is divided by partitions into several sections to accommodate a set of components and tools for external osteosynthesis. It contains (FIG. 2) polyfunctional single units 4, plates 5, rods and pins 6, beams 7, hardware 8, and tools 9. All kit components are marked for convenient recognition.

1. Polyfunctional single units 4 (MP 20.5 and MP 20.4) are designed to form a mounting assembly between the supporting beam and the bone anchor, or between the radial plate and the fixing rod. Depending on the size of an operated animal, the diameter of a hole in the single unit and the method of fastening make it possible to fix the supporting beam of 0.8 to 5.0 mm in diameter. Diameter of the bone anchor also ranges from 0.8 mm to 5.0 mm. When two single units are combined with the aid of the supporting beam, the arrangement with two degrees of freedom is formed which allows to insert the bone anchor at different angles and in different planes. The single unit design is the original development (see Patent #76446, Ukraine).

2. Plates 5 (see Patent #70025, Ukraine)

2.1. Reconstruction plates (RPSSH-5, RPSSH-7, and RPSSH-9) are used in external osteosynthesis. They are used with large and medium-size dogs, and have 5-9 holes for fixing screws Features of reconstruction plates:
Low contact with tissue
Ability to fit different bone profile
Three-point bone fixation with a single screw
Solid stiffening rib over all fasteners
Absolute stability with a single fixation point
Compression capability due to different density (tension in the thread-bone system)
Significant antirotational capability
The same type of plates can be used in animals with different weight due to doubling the thickness of the plate in hazardous fracture areas 2.2. Radial plates (PR-7 and PR-9) are designed to form monolateral, double plane and arc-ring sets of medium-small, medium and large diameter (up to 110 mm) with the use of polyfunctional single units.

3. Rods and Pins:

3.1. A self-tapping fixing rod (SFS 100.5) is designed for fixating in the bone at an angle with capturing the cortical plates.

3.2. A self-tapping fixing rod (SFS 100.5.30) is used as the main anchor in arc-ring, bilateral, momolateral and large-size structures.

3.3. A fixing, one-side sharpened rod (SFS 100.3.0) is designed for transosseous and intraosseous insertion in small- and large-size structures.

3.4. A fixing, one-side sharpened rod (SFS 100.2.2) is designed for transosseous and intraosseous insertion in small- and medium-size structures.

3.5. A fixing, one-side sharpened rod (SFS 100.2.06) is designed for transosseous and intraosseous insertion in small-size structures.

3.6. A fixing, one-side sharpened rod (SFS 100.1.6) is designed for transosseous and intraosseous insertion in small-size structures.

3.7. A fixing, one-side sharpened rod (SFS 100.1.0) is designed for transosseous and intraosseous insertion in small-size structures.

3.8. A transosseous, one-side sharpened pin (ST-150.1.6) is used for transosseous insertion with the possibility of tension.

4. Beams 4.1. A supporting beam (BO 200.5, BO 150.5, and BO 100.5):

It is used to form a stiffening rib and to support single units upon installation of monolateral and arc-ring devices compatible with the length of a limb. The stiffening rib is strengthened due to additional fixation in the single unit. The stiffening rib is strengthened upon additional arrangement with two or three beams connected through the single units.

4.2. Supporting beam (BO 50.5)

It is used to form a stiffening rib and to support single units upon installation of monolateral and arc-ring devices. The supporting bean is extended due to additional fixation in the single unit (MP 20.5).

4.3. Supporting beam (BO 30.5)

It is designed for connecting the single units (MP 20.5, MP 20.4), and also forms a short lever arm between the radial plates (PR7, PR9).

4.4. Supporting beam (BO 15.5)

It is designed for connecting the single units (MP 20.4), and also is used for fastening the single unit (MP 20.5) to the radial plates (PR7, PR9).

5. Hardware 5.1. Stabilizing screw (SSH 25, SSH 20)

It is used to fix reconstruction plates. Due to a fragment with metric thread, it makes an integral unit with the plate with the maximum rigidity.

5.2. Screw for fixation of VF plates

It is used for connecting the reconstruction plate when it is needed to increase plate thickness in the area of increased load, or when the area of fixation must be expanded.

5.3. Screw

It is used for fixing in the single unit MP 20.5 and MP 20.4.

5.4. Nut

It is used to fasten a supporting structure

6. Tools 6.1. A wrench with scratch-resistant coating which is a special wrench for assembly and installation of the system.

6.2. Drill 3*100 and drill 2*85

SHORT DESCRIPTION OF DRAWINGS

Figure 2:
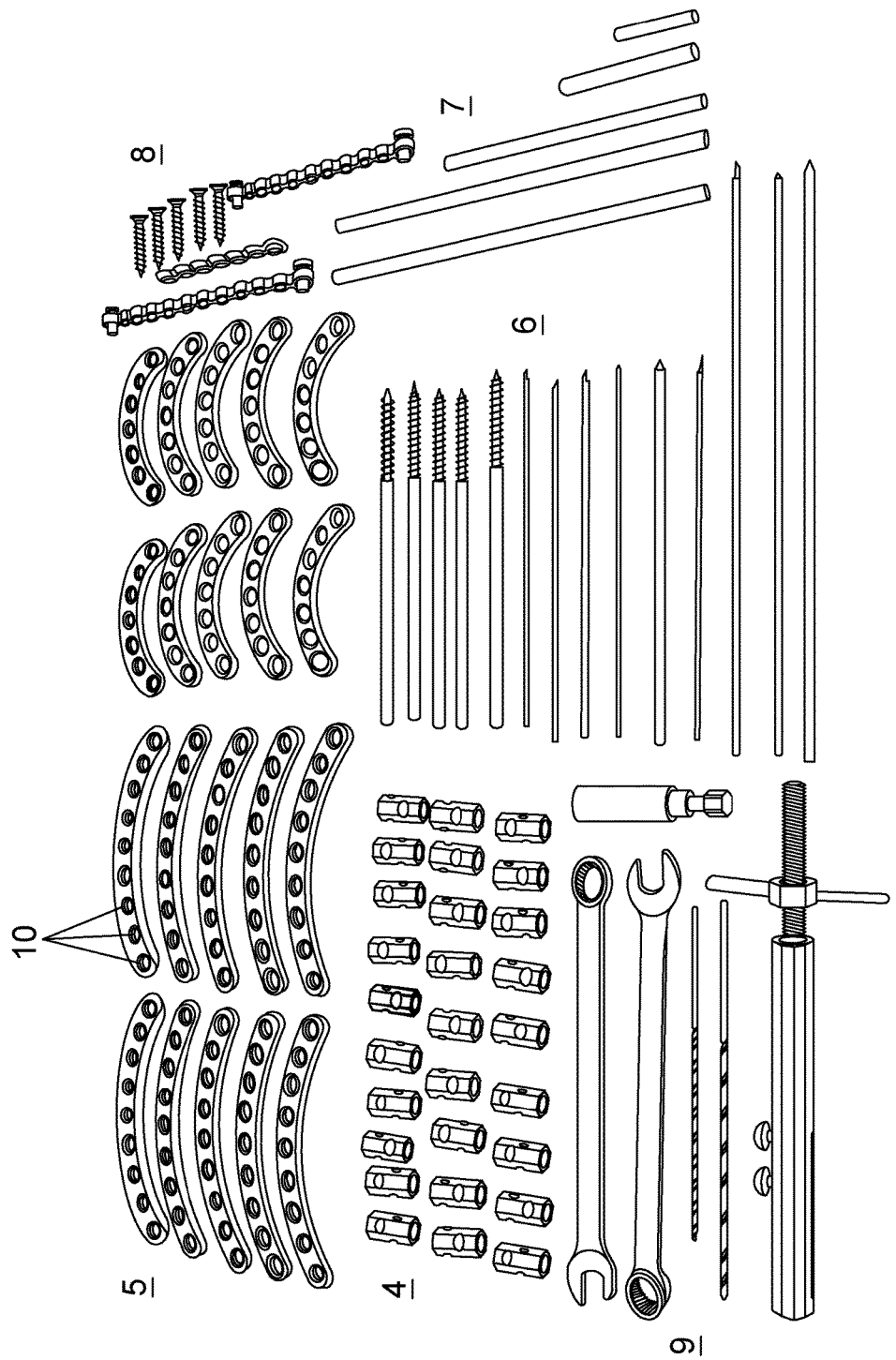

FIG. 1 gives the general view of the veterinary orthopedic device;

FIG. 2 shows a list of components of the veterinary orthopedic device.

BEST EMBODIMENT OF INVENTION

The veterinary orthopedic device is set to be used as follows. A specialist who has this kit and who was properly trained, when a clinical case occurs, shall use for an animal the suggested orthopedic products in either configuration justified by the clinical case. For example, after preparing the operated limb (fur shaving, washing), anesthetic was administered to the animal. The operation field was treated and closed reduction of fragment was performed. Two rods 6 were inserted into the bone into proximal and distal epiphyses. The rods 6 were fastened in the single unit 4, moderate compression was applied to the site of the fracture, and additional anchors were inserted. Diameter of the inserted anchors was selected according to size of the animals, and the single unit 4 was used as the anchor holder. When the radial plates 5 were used, at first the system was installed, then manual fragment reduction was performed, and after that the rods were inserted. The single unit 4 was used as the anchor holder.

The invention claimed is:

1. A veterinary orthopedic kit comprising:
a rectangular container made in the form of a box with a lid comprising a plurality of sections, wherein the rectangular container further comprises:
a plurality of polyfunctional single units;
a plurality of beams;
a plurality of plates having a plurality of holes; and
a plurality of rods and pins;
wherein the plurality of polyfunctional single units form a mounting assembly between the plurality of plates, and the plurality of rods and pins,
wherein the plurality of beams is are adapted to form a stiffening rib that supports the polyfunctional single unit with respect to a damaged limb,
wherein the plurality of plates are coupled with the plurality of polyfunctional single units to form a monolateral, double plane and arc-ring set, and
wherein the plurality of rods and pins are adapted to fix bones in transosseous and intraosseous insertions of bones, wherein two polyfunctional single units are combined with the aid of the plurality of beams that forms a two degree of freedom, wherein the two degree of freedom allows insertion of a bone anchor comprising the plurality of rods and pins at different angles and in different planes for external treatment and restoration of a damaged limb.

2. The veterinary orthopedic kit of claim 1, wherein the plurality of beams ranges between 0.8 mm to 5.0 mm in diameter.

3. The veterinary orthopedic kit of claim 1, wherein the plurality of plates are coupled with the plurality of polyfunctional single units to form a monolateral, double plane and arc-ring sets of up to 110 mm.

4. The veterinary orthopedic kit of claim 1, wherein the plurality of beams are supporting beams.

5. The veterinary orthopedic kit of claim 1, wherein the plurality of plates having a plurality of holes is selected from reconstruction plates and radial plates.

6. The veterinary orthopedic kit of claim 1, wherein the rods in the plurality of rods and pins are self-tapping fixing rods designed for fixating in the bone at an angle.

* * * * *